United States Patent [19]
Lo et al.

[11] Patent Number: 5,741,682
[45] Date of Patent: Apr. 21, 1998

[54] EXPRESSION INDUCTION METHOD

[75] Inventors: Kin-Ming Lo, Wellesley; Stephen D. Gillies, Hingham, both of Mass.

[73] Assignee: Abbott Biotech, Inc., Abbott Park, Ill.

[21] Appl. No.: 376,073

[22] Filed: Jan. 20, 1995

Related U.S. Application Data

[63] Continuation of Ser. No. 926,143, Aug. 5, 1992, abandoned, which is a continuation of Ser. No. 660,925, Feb. 27, 1991, abandoned, which is a continuation of Ser. No. 511,998, Apr. 13, 1990, abandoned, which is a continuation of Ser. No. 281,833, Dec. 8, 1988, abandoned.

[51] Int. Cl.$^6$ .............................. C12N 5/18; C12N 15/63
[52] U.S. Cl. ........................................ 435/172.3; 435/240.2
[58] Field of Search ............................. 435/69.6, 70.21, 435/240.27, 69.1, 172.3, 240.2, 320.1; 935/33, 42, 54

[56] References Cited

U.S. PATENT DOCUMENTS

| | | | |
|---|---|---|---|
| 4,399,216 | 8/1983 | Axel et al. | 435/6 |
| 4,442,203 | 4/1984 | Varshavsky | 435/6 |
| 4,656,134 | 4/1987 | Ringold | 435/69.1 |
| 4,663,281 | 5/1987 | Gillies et al. | 435/69.1 |
| 4,740,461 | 4/1988 | Kaufman | 435/69.1 |
| 4,766,075 | 8/1988 | Goeddel | 435/240.2 |
| 4,965,196 | 10/1990 | Levinson et al. | 435/69.1 |

FOREIGN PATENT DOCUMENTS

| | | |
|---|---|---|
| 0117059 | 1/1984 | European Pat. Off. |
| 0246049 | 5/1987 | European Pat. Off. |
| 0237157 | 9/1987 | European Pat. Off. ........ C12N 15/00 |
| 8606409 | 11/1986 | WIPO |
| 8704462 | 7/1987 | WIPO |

OTHER PUBLICATIONS

Dorai et al., *Journal Immunology*, 139:4232 (Dec. 1987).
Bastow et al. (1984) Adv. Enzyme Reg. 22:15–26.
Will et al. (1986) Molecular Pharmacology 29:643–648.
Schimke (1988) The Journal of Biological Chemistry 263(13):5989–5992.
Tufts University Biotechnology Engineering Center Short Course (1987).
Corin R E et al 1986 Biochemistry 25:3768–3773.
Domin et al. (1982) Molecular Pharmacology 21:478–482.
Domin et al. (1983) Cancer Research 43:2155–2158.
Bastow et al. (1984) in *Advances in Enzyme Regulation*, vol. 22 (Weber, G. ed.) Pergaman Press, NY, NY. pp. 15–26.
Southern (1975) J. Mol. Biol. 98:503–517.
Chang et al. (1976) Cell 7:391–396.
Johnson et al. (1978) J. Cell. Physiol. 97:397–406.
Nunberg et al. (1978) Proc. Natl. Acad. Sci. USA 75(11):5553–5556.
Alt et al. (1978) The Journal of Biological Chemistry 253(5):1357–1370.
Schmike et al. (1978) Science 202:1051–1055.
Wahl et al. (1979) The Journal of Biological Chemistry 254(17):8679–8689.
Kaufman et al. (1979) Proc. Natl. Acad. Sci. USA 76:5669–5673.

(List continued on next page.)

*Primary Examiner*—David Guzo
*Attorney, Agent, or Firm*—Testa, Hurwitz & Thibeault

[57] ABSTRACT

Disclosed is a method of producing increased amounts of a protein of interest in a cell by induction. The method includes transfecting a cell with multiple copies of an expression vector, each copy of which includes an expressible gene encoding an enzymatically functional dihydrofolate reductase (DHFR) and an expressible gene encoding a protein of interest. Transfected cells are cultured in the presence of methotrexate (MTX) to produce a plurality of clones. A clone containing plural copy number of the vectors which co-express DHFR and the protein of interest is then selected and cultured. The cultured clone is treated with MTX to enhance the expression of the protein of interest by inducing an increase in transcription without substantially amplifying the genes encoding the protein of interest and DHFR.

20 Claims, 9 Drawing Sheets

OTHER PUBLICATIONS

Kellems et al. (1979) The Journal of Biological Chemistry 254(2):309–318.

Thomas (1980) Proc. Natl. Acad. Sci. USA 77(9):5201–5205.

Sandri–Goldin et al. (1981) Molecular and Cellular Biology 1(8):743–752.

Ringold et al. (1981) Journal of Molecular and Applied Genetics 1(3):165–175.

Christman et al. (1982) Proc. Natl. Acad. Sci. USA 79:1815–1819.

Kaufman et al. (1982) J. Mol. Biol. 159:601–621.

Maniatis et al. (1982) *Molecular Cloning*, Cold Spring Harbor Laboratory, pp. 197–281.

Dolnick et al. (1983) The Journal of Biological Chemistry 258(21):13299–13306.

Gubler et al. (1983) Gene 25:263–269.

Simonsen et al. (1983) Proc. Natl. Acad. Sci. USA 80:2495–2499.

Gillies et al. (1983) Cell 33:717–728.

Santiago et al. (1984) Journal of Cellular Physiology 118:79–86.

Kaufman et al. (1985) Molecular and Cellular Biology 5(7):1750–1759.

Page (1985) Gene 37:139–144.

McIvor et al. (1985) Molecular and Cellular Biology 5(6):1349–1357.

Dorai et al., *Journal of Immunology*, 139:4232 (Dec. 1987).

```
                            TaqI
   Fnu4HI          val arg pro leu asn cys ile val ala
CGCTGCCATC ATG     GTT CGA CCA TTG AAC TGC ATC GTC GCC leu
10                                        20        T
val ser gln asn met gly ile gly lys asn gly asp arg
GTG TCC CAA AAT ATG GGG ATT GGC AAG AAC GGA GAC CGA 30
pro trp pro pro leu arg asn glu phe lys tyr phe gln
CCC TGG CCT CCG CTC AGG AAC GAG TTC AAG TAC TTC CAA 40                        HinfI
arg met thr thr thr ser ser val glu gly lys gln asn
AGA ATG ACC ACA ACC TCT TCA GTG GAA GGT AAA CAG AAT 50                                          60
leu val ile met gly arg lys thr trp phe ser ile pro
CTG GTG ATT ATG GGT AGG AAA ACC TGG TTC TCC ATT CCT TaqI                    70
glu lys asn arg pro leu lys asp arg ile asn ile val
GAG AAG AAT CGA CCT TTA AAG GAC AGA ATT AAT ATA GTT 80
leu ser arg glu leu lys glu pro pro arg gly ala his
CTC AGT AGA GAA CTC AAA GAA CCA CCA CGA GGA GCT CAT 90                                      100
phe leu ala lys ser leu asp asp ala leu arg leu ile
TTT CTT GCC AAA AGT TTG GAT GAT GCC TTA AGA CTT ATT 110
glu gln pro glu leu ala ser lys val asp met val trp
GAA CAA CCG GAA TTG GCA AGT AAA GTA GAC ATG GTT TGG
```

Fig. 3A

```
                                  120
ile val gly gly ser ser val tyr gln glu ala met asn
ATA GTC GGA GGC AGT TCT GTT TAC CAG GAA GCC ATG AAT 130
gln pro gly his leu arg leu phe val thr arg ile met
CAA CCA GGC CAC CTC AGA CTC TTT GTG ACA AGG ATC ATG 140                                           150
gln glu phe glu ser asp thr phe phe pro glu ile asp
CAG GAA TTT GAA AGT GAC ACG TTT TTC CCA GAA ATT GAT 160
leu gly lys tyr lys leu leu pro glu tyr pro gly val
TTG GGG AAA TAT AAA CTT CTC CCA GAA TAC CCA GGC GTC 170
leu ser glu val gln glu glu lys gly ile lys tyr lys
CTC TCT GAG GTC CAG GAG GAA AAA GGC ATC AAG TAT AAG 180                 186
phe glu val tyr glu lys lys asp OC
TTT GAA CTC TAC GAG AAG AAA GAC TAA CAGGAAGATGCTTTC

AAGTTCTCTGCTCCCCTCCTAAAGCTATGCATTTTTATAAGACCATGGGAC

BglII
TTTTGCTGGCTTTAGATCTATGAGTAATTATTTCTTTAGGGAGGGGTAGTT
```

Fig. 3B

EXPRESSION INDUCTION METHOD

This is a continuation of application Ser. No. 07/926,143 filed on Aug. 5, 1992 now abandoned which is a continuation of Ser. No. 07/660,925, filed Feb. 27, 1991, now abandoned, which is a continuation of Ser. No. 07/511,998, filed Apr. 13, 1990, now abandoned, which is a continuation of Ser. No. 07/281,833, filed Dec. 8, 1988, now abandoned.

BACKGROUND OF THE INVENTION

This invention relates to methods of protein production, and in particular, to recombinant methods of enhancing protein production.

Eucaryotic cell culture is the preferred system for producing large and complex mammalian proteins because eucaryotic cells are able to perform post-translational modifications (e.g., glycosylation) required for the activity of many of these proteins. However, eucaryotic cell lines normally do not exhibit the level of protein expression of which many prokaryotes are capable. Therefore, methods have been developed to generate engineered eucaryotic cell lines which express higher levels of heterologous proteins.

One known system exploits the ability of cells to co-amplify the copy number of integrated DNA encoding a marker gene and a gene encoding the protein of interest. This system includes the use of the dihydrofolate reductase (DHFR) gene as the marker gene and methotrexate (MTX), a folate analog which inhibits the activity of DHFR (see, for example, U.S. Pat. No. 4,656,134 and U.S. Pat. No. 4,399,216).

DHFR is an enzyme which catalyzes the conversion of folate to tetrahydrofolate, a requisite substance in a number of biosynthetic pathways in the body. Cells deficient in DHFR (DHFR(−)) require the supplementation of a number of metabolites to their media for survival and growth. Alternatively, a DHFR gene can be transfected into the DHFR(−) host. Cells wild type for DHFR have a high mortality rate if they are cultured in the presence of even low concentrations of MTX. MTX binds to and inhibits DHFR stoichiometrically, thereby leading to cell death. However, a small percentage of the cells survive despite the presence of the inhibitor (Schimke et al. (1978) Science 202:1051–1055). These cells have been found to contain an amplified number of DHFR genes, and an equivalent increase in the level of intracellular DHFR. By repeated exposure to progressively higher concentrations of MTX, a cell culture which may initially be killed by 50 nM MTX can eventually survive in 500 µM MTX. These cells may contain a high copy number of integrated DHFR genes (e.g., several thousand copies), accompanied by an equally elevated level of intracellular DHFR.

It has been discovered that regions flanking the DHFR gene in the expression vector may be co-transfected and co-amplified as well (Kaufman et al., (1985) Molec. Cell Biol. 5:1750–1759). In the case where this flanking region contains a gene encoding a protein of interest, co-amplification may result in a much elevated intracellular level of this protein of interest as well (Alt et al. (1978) J. Biol. Chem. 253:1357–1370; U.S. Pat. No. 4,656,134; and U.S. Pat. No. 4,399,216).

Generally, gene amplification can only be achieved by stepwise selection of resistant cells in increasing concentration of drugs. In addition, gene amplification is a rare event. It usually takes several weeks for surviving cells to form colonies and to adapt to a two to five fold increase in MTX concentration. The complete amplification process, including the adaptation of a cell line from 50 nM MTX to 500 µM MTX, can take many months, making it a time-consuming and tedious process.

In addition, amplified genes may not be maintained indefinitely. In cells maintained under constant selection, the amplified DNA sequences or genes are undergoing continual changes, and can be classified as stable or unstable. Unstable amplified genes often reside on small, self-replicating extrachromosomal elements called double minute chromosomes (Kaufman et al. (1979) Proc. Natl. Acad. Sci. (USA) 76:5669–5673). Because double minute chromosomes lack centromeres, they are not equally segregated into daughter cells at mitosis. Therefore, in the absence of selection, the cell population can lose half of its amplified genes in as few as 20 cell doublings (Schimke, (1988) J. Biol. Chem. 263:5989–5992). Stable amplified genes are often associated with chromosomal regions called homogeneously staining regions (Numberg et al. (1978) Proc. Natl. Acad. Sci. (USA) 75:5553–5556). However, in the absence of continued selection, even stably integrated amplified sequences are variably unstable. For example, when stable cell lines are grown in the absence of MTX, they can lose their amplified genes over a period of 6 to 12 months.

It is an object of the present invention to provide a method of increasing the expression of a protein(s) of interest in cultured bioengineered cells. It is another object to provide a method of enhancing protein expression in mammalian cells which will not be lost over time and which does not involve gene amplification. An additional object is to provide a method of inducing protein expression in a cell culture which can be accomplished more rapidly than can amplification (i.e., in weeks instead of months).

SUMMARY OF THE INVENTION

This invention provides methods of increasing the production of a protein of interest in eucaryotic cells. More specifically, the invention relates to methods of increasing protein expression in the absence of gene amplification using various genetic engineering, transfection, culturing and induction methods.

The term "induction" as used herein refers to an increase in the rate of transcription, and subsequently in translation, in the absence of substantial (no greater than about 2- or 3-fold) gene amplification. "DHFR mutein" refers to a mutant or analog form of dihydrofolate reductase which has wild type enzymatic activity but reduced methotrexate (MTX)-binding affinity relative to wild type DHFR. "Protein of interest" refers to a protein or active fragment or analog thereof expressed by the transfected wild type host cell which is to be harvested for subsequent use.

Myeloma cells can be transfected so as to contain a very high copy number of integrated plasmids or expression vectors. It has been discovered that if these vectors are bioengineered to contain a marker gene encoding a mutein of DHFR, then exposure of the initial high copy number clones to MTX can result in the induction of a very high level of expression of the gene(s) of interest which were co-transfected with the marker gene.

Further, these initial clones adapt to a 100 to 1000-fold stepwise increase in MTX concentration in a few weeks, during which the expression of the gene of interest, but not their copy number, increases several-fold. In addition, cells adapted to a high concentration of MTX (e.g., 5 µM) can be grown in media containing low concentration of MTX or even in MTX-free media. In such media, the growth rate and viability of the cells are substantially improved, although this response is accompanied by a drop in expression level. A cell population cultured in such a medium can be reinduced to its original high level of expression by adding MTX back to the medium.

The invention exploits these discoveries to provide a process for producing enhanced quantities of a protein of interest, and transfectomas which may be induced to produce such materials. In accordance with the invention, a cell is transfected with multiple copies of an expression vector, each copy of which includes both an expressible gene encoding an enzymatically functional DHFR, and an expressible gene encoding a protein of interest. Transfected cells are cultured in the presence of MTX to produce a plurality of clones. A clone is then selected which contains a plural copy number of the transfected vector and which co-expresses DHFR and the protein of interest. This clone is then cultured for large scale growth in media containing little or no MTX. At the desired volume of cells and optimal cell density, the cells are then treated with MTX to enhance the expression of the protein of interest by inducing an increase in transcription without substantially amplifying the genes encoding the protein of interest and DHFR.

Preferably the DHFR is a mutein that has reduced MTX-binding affinity relative to wild type DHFR, and the cell to be transfected contains a wild type DHFR gene such as a myeloma, for example, of murine origin, such as one from the Sp2/0 line.

The preferred method of transfection is protoplast or spheroplast fusion, which yields high copy number of the integrated expression vector.

Expression vectors useful in the practice of the invention have a first and second transcription unit containing a marker gene and a gene encoding a protein of interest, respectively. The marker gene preferably encodes a mutein of DHFR which displays wild type enzymatic activity, but reduced MTX-binding affinity relative to wild type DHFR (e.g., 3T6-R400; Simonsen and Levinson (1983) Proc. Natl. Acad. Sci. (USA) 80:2495–2499). This gene may be under the transcriptional control of, for example, the SV40 early region.

The protein of interest, encoded by a gene on the second transcription unit, may be any protein expressible in eucaryotes. Such a protein may be useful for correcting a condition or deficiency, such as those encoding peptide hormones, interleukins, tissue plasminogen activator (tPA), pro-urokinase (pro-UK), the heavy or light chains of human or murine immunoglobulins, chimeric mouse-human immunoglobulins, or active analogs, derivatives, fragments, or fusion products thereof. The second transcription unit may also contain an enhancer element which is preferably derived from the heavy chain of the immunoglobulin gene (Gillies et al. (1983) Cell 33:717–728; U.S. Pat. No. 4,663,281), and a promoter. Useful promoters for the second transcription unit are strong promoters such as the metallothionein promoter, the kappa light chain promoter, or the SV-40 promoter. A promoter may be referred to as being strong or weak depending on the number of mRNAs initiated per unit time.

The two transcription units containing the DHFR gene and the gene of interest may be separated by a piece of DNA which serves as a blocking element (Gillies et al., co-pending U.S. patent application Ser. No. 837,595, filed Mar. 7, 1986 now U.S. application Ser. No. 08/223,381), i.e., a promoter having the effect of blocking the action of the enhancer on the DHFR mutein transcription unit. The λ light chain promoter is particularly useful for this purpose.

In a preferred aspect of the invention the selected clone is treated with serially increasing concentrations of MTX, for example, in the range of about 0.1 to 100 μM. However, any concentration range of MTX which will enhance the expression of the protein of interest by about 4- to 8-fold in less than 10 cycles of cell division is useful.

BRIEF DESCRIPTION OF THE DRAWING

The foregoing and other objects of this invention, the various features thereof, as well as the invention itself may be more fully understood from the following description, when read together with the accompanying drawings in which:

FIG. 3 is a schematic representation of the nucleotide sequence and corresponding amino acid sequence of 3T6-R400 mutein DHFR, the preferred mutein form for use in the invention;

DESCRIPTION OF THE INVENTION

This invention relates to methods of inducing a high level of gene expression without substantial gene amplification in stable, mitotically competent eucaryotic cell cultures.

It has been discovered that initial clones cultured from cells transfected with plural copies of vectors comprising a mutant DHFR gene and a gene encoding a protein of interest, if selected in the presence of 100 nM MTX, produce a high level of the protein of interest (1–5 μg/$10^6$ cells/day), and that such clones adapt to a 100 to 1000-fold increase in MTX concentration quickly (a few weeks), during which the expression of the gene of interest increases several-fold.

Furthermore, cells adapted to a high concentration of MTX (e.g. 5 μM) can be grown in media containing low concentration of MTX or even in MTX-free media. In such media, the growth rate and viability of the cells are substantially improved, although this response is accompanied by a drop in expression level. A cell population from such media can be reinduced to its original high level of expression by adding MTX back to the media.

Figure 1:
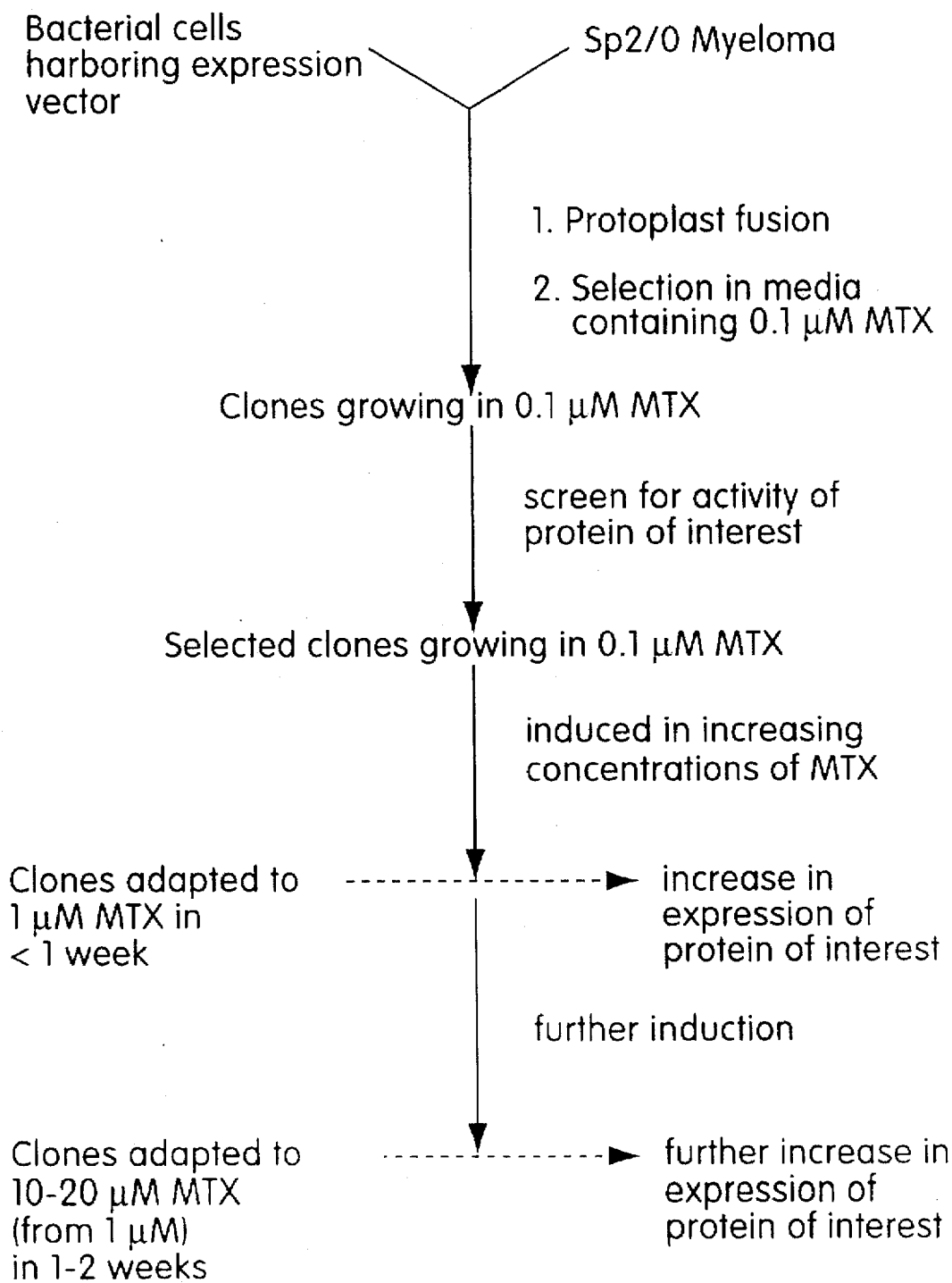
FIG. 1 is a diagrammatic representation of the method of the present invention.

The foregoing discovery may be exploited to produce cultures of transformants having excellent expression levels of any desired protein using conventional recombinant DNA technology. As depicted in FIG. 1, the process involves production of an expression vector, using any known technique, of a type encoding two transcription units. The "marker" gene transcription unit comprises at least a promoter and a gene encoding a DHFR mutein which has enzymatic activity characteristic of wild type DHFR, but reduced binding to MTX. The other transcription unit encodes a protein of interest, which may be any protein expressible by the intended host cell. This vector is then transfected into an animal cell host. Excellent results have been achieved using murine myeloma cells as the host, although any continuous animal cell may be used, (e.g., Chinese hamster ovary cells). The transfection must be conducted under conditions which result in plural copies of the vector integrating into individual cells of the host. Towards this end, known protoplast or spheroplast fusion techniques are preferred.

Next, the cells are cultured in the presence of MTX and screened for clones exhibiting high expressions of the protein of interest. The selected clones are then cultured to densities suitable for protein production. If desired, these may be reexposed to MTX to repeatedly induce expression of the protein of interest.

Details of specific implementation of the foregoing procedure, and disclosure of the best mode of practicing the invention, are disclosed below.

The invention will be further understood from the following, non-limiting examples.

EXAMPLES

1. Isolation of Full-Length cDNA Encoding tPA and UK

TPA-poly[A$^+$] mRNA and UK-poly[A$^+$] mRNA are isolated from the Bowes melanoma cell line and the epithelial cell line A431, respectively by established methods (see, e.g., Maniatis et al., (1982) *Molecular Cloning, A Cloning Manual*, Cold Spring Harbor Laboratory, pp. 197–198). Synthesis of double-stranded cDNA is performed essentially as described by Gubler and Hoffman (1983) Gene 25:263–269, herein incorporated as reference. Following linker ligation, the cDNA is cloned into λgt 10. The phage libraries are then screened with oligonucleotide probes. Full-length cDNAs, as determined by sequencing, are cloned into the XhoI site of the expression vector.

2. Construction of Expression Vectors

Figure 2:
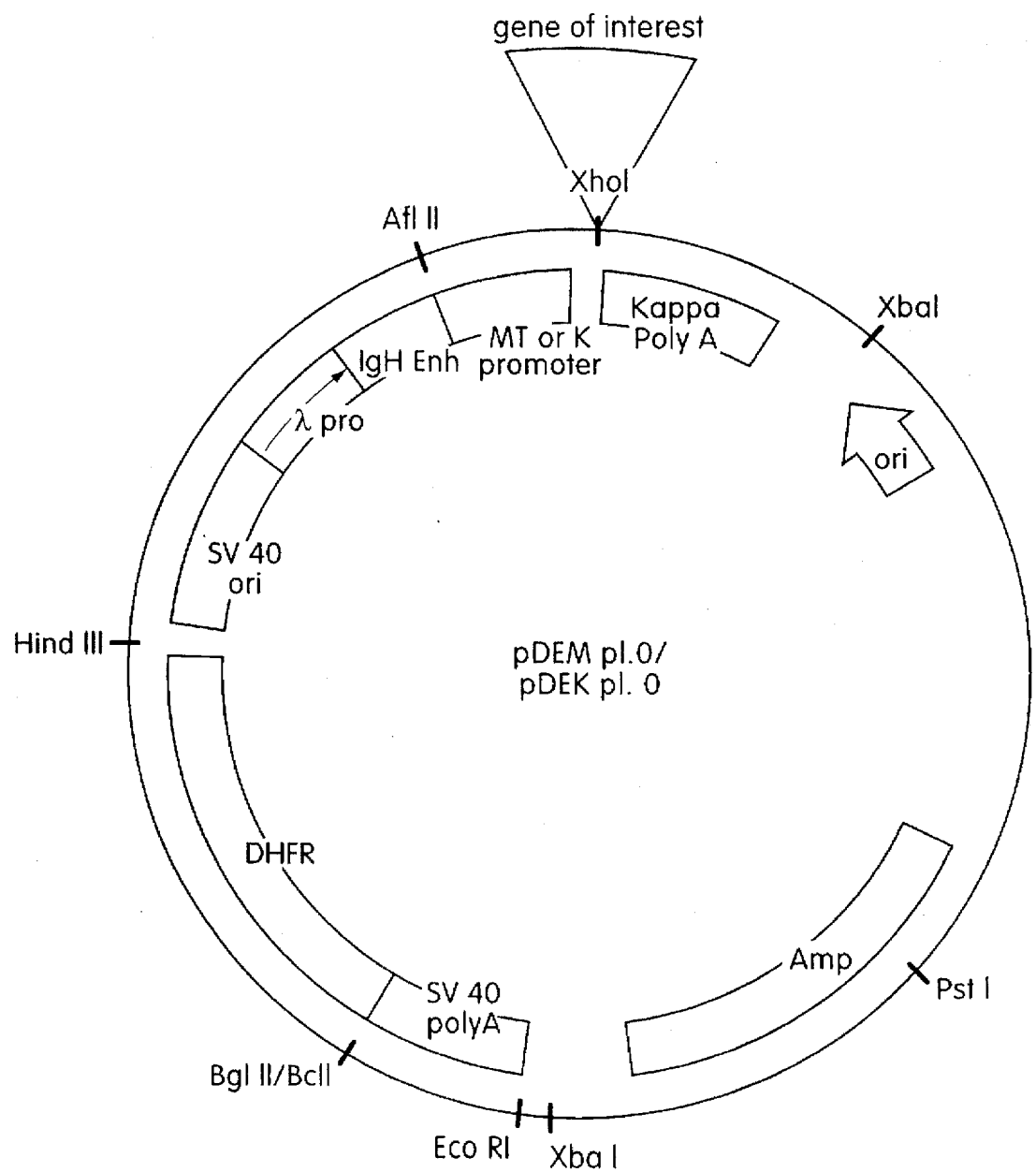
FIG. 2 is a schematic representation of a vector construction useful for transfection of murine Sp2/0 hybridoma cells; the cDNA of interest is inserted into the XhoI site of the vector.

The expression vector pDEMp 1.0 (FIG. 2) is derived from the expression vector pEMp 1.0. The construction of pEMp 1.0 is accomplished essentially as described by Gillies in co-pending patent application Ser. No. 066,727, filed Jun. 25, 1987, now abandoned, herein incorporated as reference. The xanthine-guanine phosphoribosyl transferase (XGPRT) gene is replaced by DHFR cDNA as the marker gene in pDEMp 1.0. The DHFR marker gene encodes an altered mouse DHFR that has a reduced binding affinity for MTX. Its complete DNA sequence (and corresponding amino acid sequence) is shown in FIG. 3. The Fnu4H1 site at the −9 position of the mouse DHFR cDNA is converted to a Hind III site via linker ligation. This Hind III site is used to place the DHFR gene under the control of the SV-40 enhancer and promoter (FIG. 2). The polyadenylation signal of the SV-40 early region is used. This is achieved by ligating the Bcl I-Bam H1 restriction fragment of SV-40 to the Bgl II site at the 3'-untranslated region of the DHFR cDNA. The Bam H1 site is in turn converted to an EcoRI site via linker ligation. Thus, the pDEMp 1.0 vector contains the Hind III-Pst I vector fragment of pEMp 1.0, a PstI-EcoRI fragment (containing part of the ampicillin resistance gene) of pBR322, and the Hind III-EcoRI fragment (containing the DHFR cDNA, and the early SV-40 polyadenylation signal).

The expression vector pDEKp 1.0 contains a synthetic kappa promoter, which replaces the metallothionein promoter in pDEMp 1.0. The synthetic kappa promoter is constructed as an AflII-XhoI fragment by ligating synthetic oligonucleotides which encode both strands of the kappa promoter of the immunoglobulin gene.

The gene of interest is cloned into the XhoI site of the expression vector. The transcription unit consists of the heavy chain enhancer of the immunoglobulin gene, the metallothionein/kappa promoter, and the polyadenylation signal of the kappa chain of the immunoglobulin gene. The transcription orientation of the gene of interest is opposite that of the DHFR marker gene, and the two transcription units are separated by a λ promoter as a blocking element. For more details concerning the blocking element, see copending patent application Ser. No. 066,727, filed Jun. 25, 1987, now abandoned, herein incorporated as reference.

3. DNA Transfection and Cell Culture

The murine hybridoma line Sp2/0 is grown in Dulbecco's Modified Eagle's Medium (DMEM) containing 10% fetal calf serum (FCS). Plasmids are propagated in *E. coli* C600R$^-$, which is used for making protoplasts. Sp2/0 cells are transfected by a modification of the protoplast fusion technique of Sandri-Goldin ((1981) Mol. Cell Biol. 1:743–752), as described by Gillies et al. ((1983) Cell 33:717–728). After transfection the cells are plated in microtiter plates at $10^4$ cells/well. Selection medium (containing 100 nM MTX) is added 24 hours later. The cells are fed with the selection medium at three-day intervals for two more times. Colonies appear 10–14 days after transfection. They are screened at the 96-well stage by ELISA or activity assay, and the selected clones expanded.

4. Protein Assays (a) ELISA:

Supernatants containing 10% FCS are removed from 96-well plates and assayed directly by tPA ELISA as described in co-pending patent application Ser. No. 066,727, filed Jun. 25, 1987, now abandoned, herein incorporated as reference.

(b) Activity Assays:

To harvest samples for activity assay, $10^6$ cells are incubated in 1 mL of media containing 1% fetal calf serum (FCS) in a 24-well plate. After 24 hours, the media is removed for assay. Activity is expressed in Iu/$10^6$ cells/day (Iu/mL).

TPA activity is monitored by an indirect assay as described in related copending U.S. patent application Ser. No. 151,707, now U.S. Pat. No. 4,929,560 herein incorporated as reference. In this procedure, plasminogen is catalytically converted to plasmin by tPA in the presence of fibrin. The cleavage of the chromogenic substrate S2251 (Helena Labs, Beaumont, Tex.) by plasmin is measured.

UK activity is assayed by the direct S-2444 assay as described in related U.S. patent application Ser. No. 205,437, now U.S. Pat. No. 4,920,051 herein incorporated as reference. In this assay, pro-UK is quantitatively converted by plasmin to UK. The amidolytic activity of UK is monitored directly by cleavage of the chromogenic substrate S-2444 (Helena #5281). Purified UK (Calibiochem. #672081) is used as standard.

5. Genomic DNA Analysis

Figure 5:
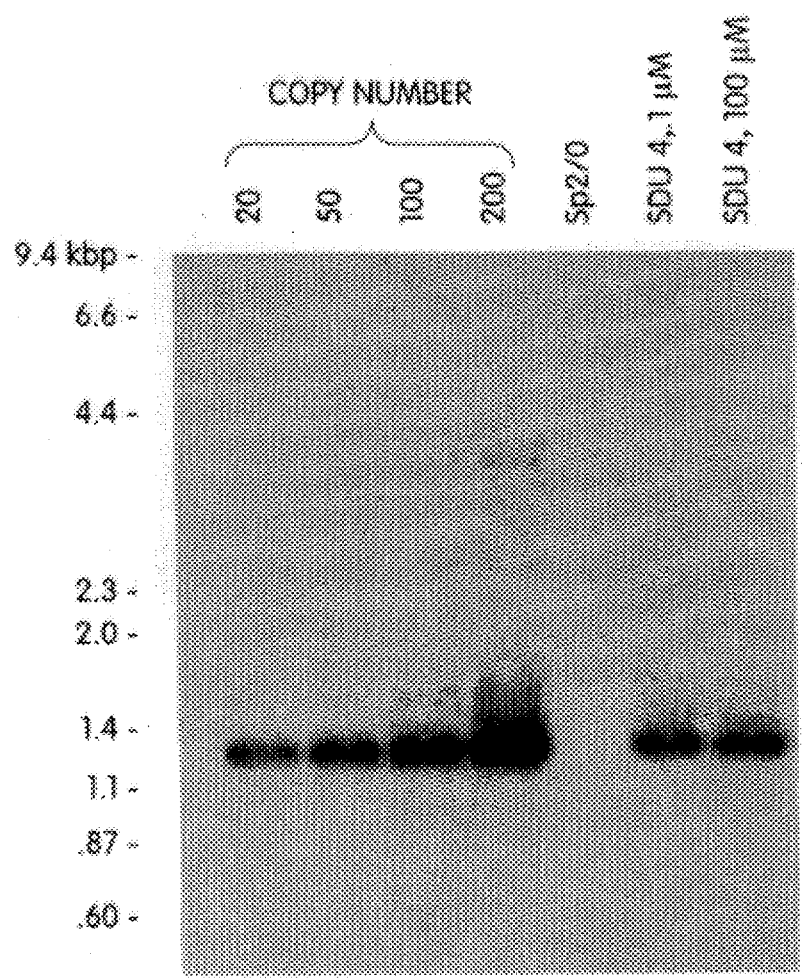
FIG. 5 is a photographic representation of an autoradiogram of a Southern blot probed with DHFR cDNA.
Figure 6:
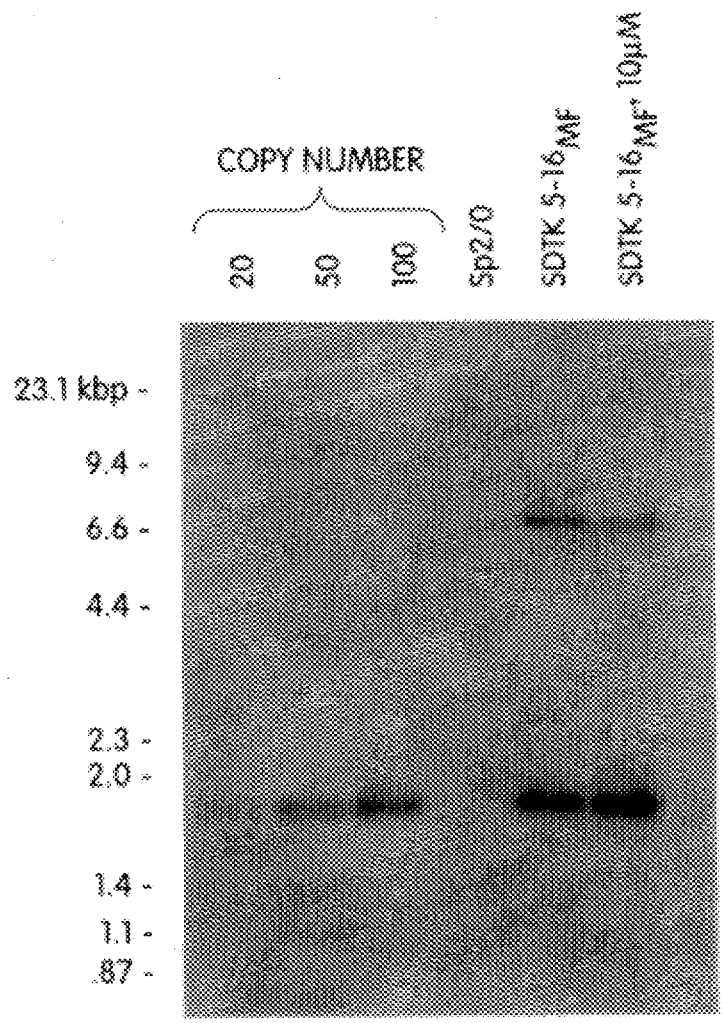
FIG. 6 is a photographic representation of an autoradiogram of a Southern blot probed with a synthetic DNA duplex corresponding to a coding region $Glu^{254}$ to $Ile^{317}$ of tPA.

High molecular weight DNA is prepared as described by Maniatis et al. (ibid. pp. 280–281). 5 μg DNA is digested to completion with the respective restriction enzymes and electrophoresed on 1% agarose gels in TAN buffer (50 mM Tris, 20 mM sodium acetate, 20 mM sodium chloride, 2 mM Na$_2$EDTA, pH 8.2). Southern blot transfer is then performed as described by Southern ((1975) J. Mol. Biol. 98:503). The DNA from the respective clones shown in FIG. 4 was digested with XhoI, electrophoresed, blotted, and then hybridized with an oligolabelled XhoI fragment containing the UK cDNA. The DNA from the respective clones shown in FIG. 5 was digested with Eco RI and SalI, electrophoresed, blotted, and then hybridized with an oligolabelled Eco RI-SalI fragment containing the DHFR cDNA. The DNA from the respective clones shown in FIG. 6 was digested with XhoI, electrophoresed, blotted, and then hybridized with an oligolabelled synthetic duplex of tPA cDNA. The DNA from the parental Sp2/0 myeloma is used as a control. In each Southern blot, digested plasmid DNA in amounts equivalent to 20, 50, 100, and 200 copies were run as copy number markers. The molecular weight standards are indicated in kilobases (kb).

6. RNA Analysis

Figure 7:
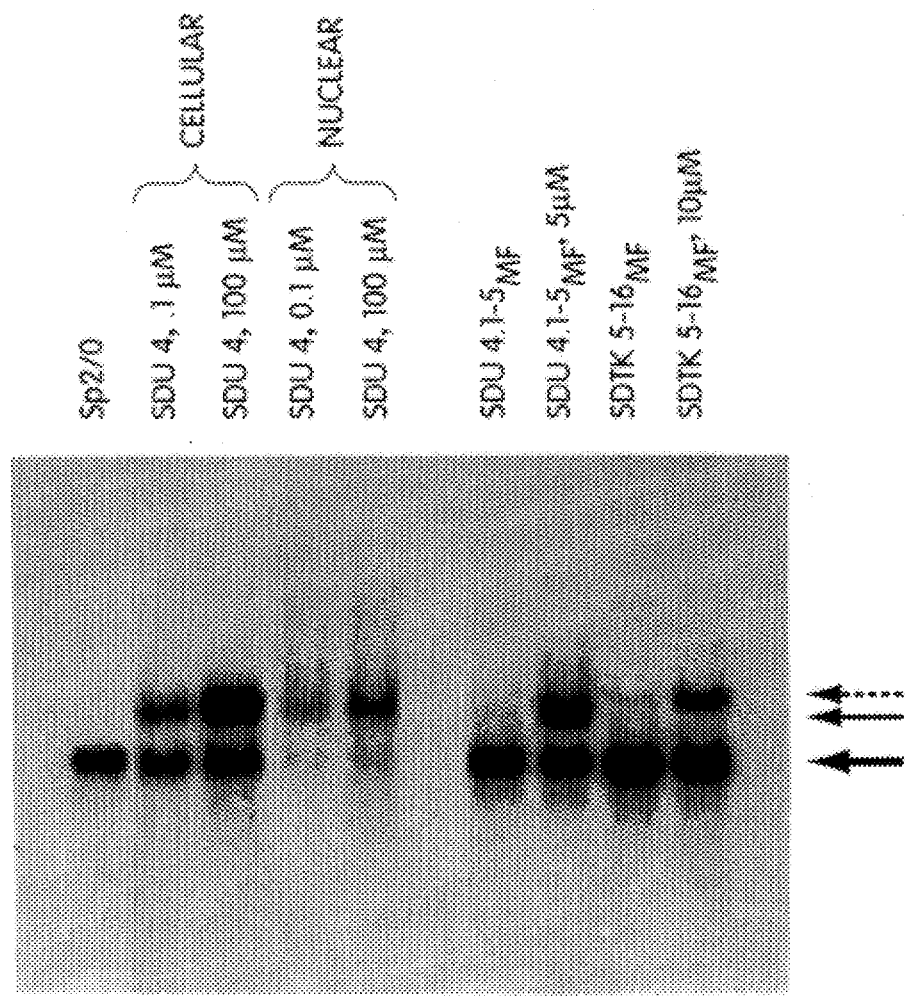
FIG. 7 is a photographic representation of an autoradiogram of a Northern blot probed with an oligolabelled 1 Kb fragment of the kappa light chain gene.
Figure 8:
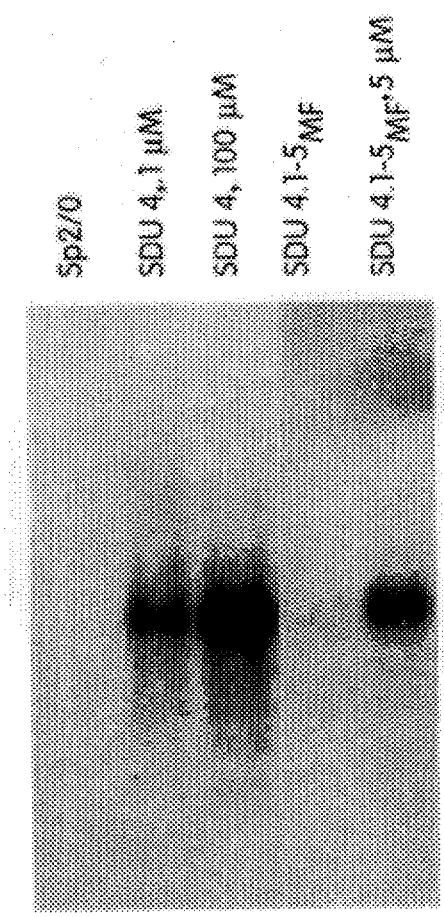
FIG. 8 is a photographic representation of an autoradiogram of a Northern blot probed with oligolabelled DHFR cDNA.

Cellular and nuclear RNA are prepared as described by Gillies et al. (Submitted, 1988). The RNA is denatured with formamide, electrophoresed on a 1.2% agarose gel in formaldehyde buffer, and transferred to nitrocellulose (Thomas (1980) Proc. Natl. Acad. Sci. 77:5201). About 0.5 μg of RNA is loaded per lane of the Northern blots shown in FIGS. 7 and 8. Except for the two lanes which contain nuclear RNA as indicated, the rest of the lanes are all cytoplasmic RNA. In FIG. 7, the amounts of cytoplasmic RNA loaded on each lane have been standardized to contain the same amount of kappa message (dark arrow), which the parent Sp2/0 makes. Both the UK message (light arrow) and the tPA message (broken arrow) contain the 3'-untranslated region of the kappa light chain and hence hybridize with the probe. The probe is an oligolabelled 1 kb fragment of the kappa light chain gene including the 3'-untranslated region. In FIG. 8, the Northern blot is probed with oligolabelled DHFR cDNA.

The RNA (and DNA in FIGS. 4-6) of the methotrexate-free (MF) subclones were prepared 6-7 weeks after the subclones have established colonies in the subcloning. At the time the RNA was prepared, the activity assays of SDU 4.1-5$_{MF}$ were 100 Iu/mL in MTX-free media and 2300 Iu/mL at 5 μM MTX respectively, and the activity assays of SDTK 5.16$_{MF}$ were 450 Iu/mL in MTX-free media and 6000 Iu/mL at 10 μM MTX respectively.

7. Gene Transfer with pDEMp 1.0

The efficiency of gene transfer into Sp2/0 cells by protoplast fusion is studied using the expression vector pDEMp 1.0-tPA. When 100 nM MTX is used for selection, the transfection frequency is about 1–2×10$^{-5}$ cells; the percentage of tPA-producing cell lines among the clones is close to 90%. The supernatant of clones in the microtiter plates have activity of 200–900 Iu/mL. Similar results are obtained with pDEMp 1.0-UK. TABLE 1 (below) shows the initial expression level of the first set of clones from protoplast fusion using the pDEMp 1.0-tPA and 1.0-UK vectors.

8. Growth and Protein Expression in Presence of Higher Concentrations of MTX

The MTX-resistant transfectomas are grown in culture media containing progressively increasing concentrations of MTX. When the cells initially selected at 100 nM MTX are subjected to 0.5 μM MTX, and then to 1 μM MTX, the cells adapt to the higher drug concentration within a week with no significant drop in viability. When the MTX concentration is raised in a stepwise fashion from 1.0 μM to 2.5 μM, then to 5 μM, 10 μM and 20 μM, etc., the viability of the cells drops to 40–70%. Generally, it takes less than two weeks for the cells to adapt to a 5-fold increase in MTX concentration. The production of tPA or UK by the cells at the various concentrations of MTX is assayed. Generally, for the high producing lines, there is a two-fold increase in expression level for a ten-fold increase in MTX concentration in the media. However, when the MTX concentration is above 20 μM, the expression level tends to level off (see TABLE 1 below).

9. Clones from Transfections with pDEKp 1.0

The transfection frequency with the expression vectors pDEKp 1.0-tPA and pDEKp 1.0-UK is only about 10 to 20% of that with pDEMp 1.0-tPA and pDEMp 1.0-UK, although the percentage of tPA and UK producing clones remains high (i.e., about 80%). The vector pDEKp 1.0 gives rise to transfectants which produce a significantly higher level of tPA/UK than can be obtained with pDEMp 1.0. When kappa clones are propagated in increasing concentrations of MTX, higher levels of expression of tPA and UK are also the result.

TABLE 1 shows activity results of tPA-producing (SDT) and UK-producing (SDU) cell lines. Clones obtained with expression vector pDEKp 1.0 have a prefix "K" before the clone number; the rest are clones obtained with pDEMp 1.0.

TABLE 1

| Clone # | Activity (in Iu/mL) [MTX] → | | | | | |
|---|---|---|---|---|---|---|
| | .1 μM | 1 μM | 5 μM | 10 μM | 20 μM | 100 μM |
| SDT 1 | 900 | 2000 | — | 4200 | — | — |
| SDT 2 | 575 | 1400 | — | 1600 | — | — |
| SDT 3 | 905 | 940 | — | 1320 | — | — |
| SDT 4 | 510 | 300 | — | 800 | — | — |
| SDT 5 | 250 | 700 | — | 1600 | — | — |
| SDT 6 | — | — | — | — | — | — |
| SDT 7 | 900 | 1000 | — | 1400 | — | — |
| SDT K-3 | 2500 | 5000 | — | — | 6500 | — |
| SDT K-5 | 4000 | 8000 | — | — | 10000 | — |
| SDU 1 | 100 | — | — | — | — | — |
| SDU 2 | 0 | — | — | — | — | — |
| SDU 3 | 500 | 700 | 1500 | — | 1600 | — |
| SDU 4 | 500 | 1200 | 2000 | — | 3500 | 4000 |
| SDU 5 | 300 | 500 | 1000 | — | — | — |
| SDU 6 | 150 | 310 | — | — | — | — |
| SDU K-6 | 1000 | 2000 | 2980 | — | — | — |
| SDU K-9 | 1000 | 2300 | 2750 | — | — | — |

10. Analysis of Gene Copy Number and RNA Level

The copy number of plasmid DNA is examined by Southern analysis (ibid.) to determine if the increase in expression level is due to amplification or induction.

The initial clones (e.g. SDU-4 and SDT-1) at 100 nM MTX already contained about 100 copies of plasmid DNA. However, SDU-4 does not show any amplification of either the introduced DHFR gene or the UK gene from 0.1 μM to 100 μM MTX (FIGS. 4 and 5), although there is an eight-fold increase in the expression of UK, as determined by assay of activity. The increase in the levels of both nuclear and cytoplasmic RNA (UK and DHFR) is evident in the Northern blots shown in FIGS. 7 and 8. A similar absence of gene amplification is also seen in clone SDT-1, from 100 nM to 10 μM MTX, despite the presence of a four-fold increase in the expression of tPA.

11. MTX-Free Subclones and Induction with MTX

When MTX is removed from the media, the expression levels of most of the clones drops to less than 50% of their original levels within the first week. To determine if the gene of interest in this surviving subpopulation has been lost, SDTK-5 growing at 1 μM MTX, and SDU4.1 (a subclone of SDU4 which expresses UK at 3,000 Iu/mL) growing a 5 μM MTX are subcloned in MTX free media. A number of MTX-free subclones are screened, and the best are selected: SDTK5-16$_{MF}$ (MF=MTX-free subclone); SDU4.1-5$_{MF}$; and SDU4.1-18$_{MF}$. Their expression levels are much lower than those of their parent clones, as shown in TABLE 2.

TABLE 2

| Subclone | Time Induced | Activity (in Iu/ml) | | |
|---|---|---|---|---|
| | | MTX Concentration | | |
| | | 0 | 1.0 μM | 5.0 μM |
| SDU4.1-5$_{MF}$ | 0 | 400 | — | — |
| | 14 hr | — | 900 | 1100 |
| | 24 hr | — | 1100 | 2200 |
| | 10 d | — | 2300 | 2250 |
| SDU4.1-18$_{MF}$ | 0 | 250 | — | — |
| | 14 hr | — | 750 | 1200 |
| | 24 hr | — | 1500 | 1600 |
| | 10 d | — | 3000 | 3300 |

MTX is then reintroduced into the media of the MTX-free subclones. SDTK5–16$_{MF}$, which is expressing about 1,000 Iu/ml in MTX-free media, is propagated for about two weeks in 1 μM MTX, and then in 10 μM for two more weeks. Expression levels are 3060 Iu/ml in 1 μM MTX and 6480 Iu/ml in 10 μM MTX.

To determine if these MTX-free subclones can be induced to a higher level of expression in a shorter period of time, SDU 4.1–5$_{MF}$ and SDU 4.1–18$_{MF}$ are cultured in growth media containing 1 μM and 5 μM MTX for 14 hours, 24 hours, and 10 days respectively. At the end of the induction period 10$^6$ cells are taken out, spun down, and put into 1 mL of normal growth media containing 1% fetal calf serum (FCS). The supernatants are harvested after 24 hours for assay. As shown in TABLE 2, the cells can be reinduced to a several fold increase in expression in as little as 14 hours, which is less than the doubling time of the cells.

Figure 4:
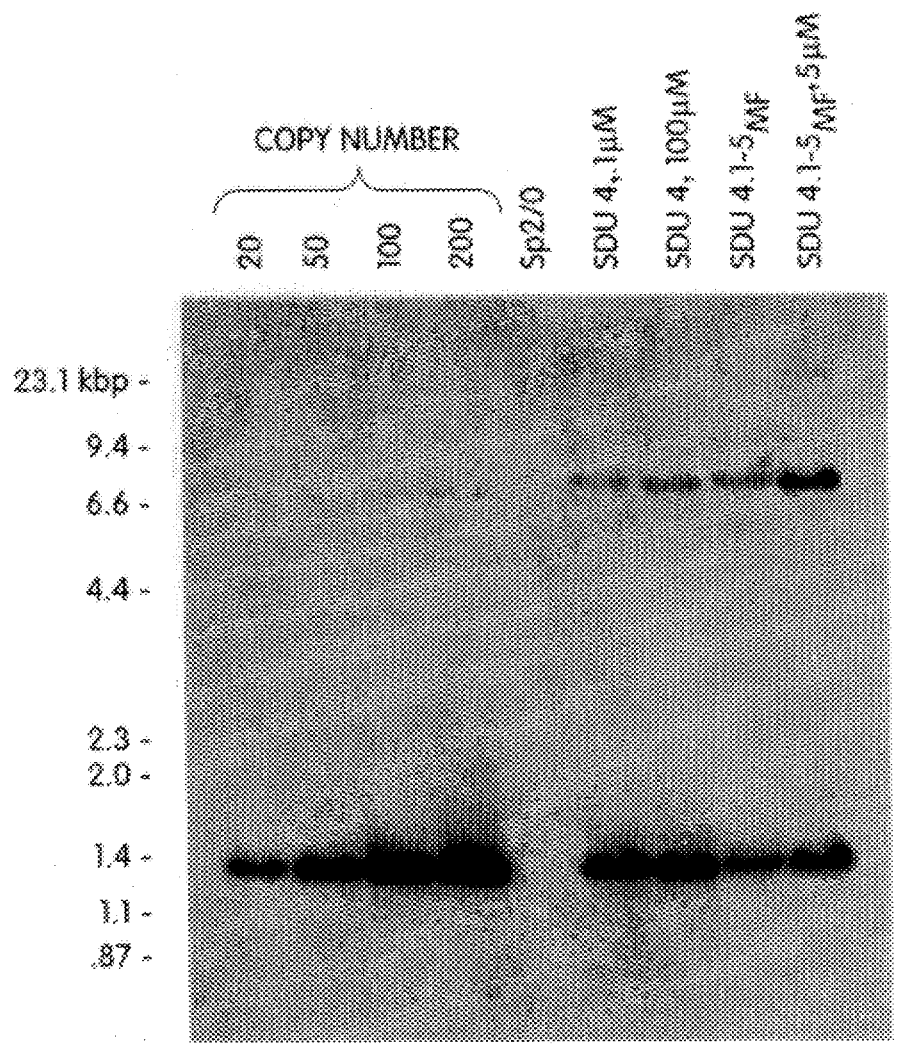
FIG. 4 is a photographic representation of an autoradiogram of a Southern blot probed with urokinase cDNA.

The induction period of 14 hours is too short for any significant gene amplification to have taken place. Therefore, to make sure that the increase in expression level is an induction phenomenon, the copy numbers of plasmid DNA of these MTX-free subclones were examined by Southern analysis. There is a lack of significant gene amplification between SDU 4.1–5$_{MF}$ growing in MTX-free media, and SDU 4.1–5$_{MF}$ growing in 5 μM MTX for about six weeks (FIG. 4). The RNA levels of UK and DHFR as determined by Northern analysis (FIGS. 7 and 8) show a drastic increase for cells growing at 5 μM MTX that cannot be explained by their relative gene copy numbers. Similarly, the SDT K5–16$_{MF}$ in MTX-free media and SDT K5–16$_{MF}$ growing in 10 μM MTX have approximately the same number of copies of plasmid DNA (FIG. 6), but there is a greater than ten-fold increase in the mRNA level of tPA when the cells are grown in 10 μM MTX.

The activity assay was performed about four weeks after SDU 4.1–5$_{MF}$ and SDU 4.18$_{MF}$ had established colonies in the process of subcloning. Since there is no selection pressure on these subclones in MTX-free media, they tend to lose their clonal homogeniety and hence their expression level over an extended period of time.

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein.

We claim:

1. A method of inducing transcription of a gene encoding a protein of interest in a host cell, said gene being present in a DHFR-selectable expression vector, comprising the steps of:

(a) contacting a mammalian cell with an expression vector comprising a first transcription unit comprising an expressible gene encoding an enzymatically functional dihydrofolate reductase (DHFR) and a second transcription unit comprising an expressible gene encoding a protein of interest, under conditions suitable for transfection of said cell with at least about 100 copies of said vector, such that a transfectant of said mammalian cell is produced;

(b) subjecting said transfectant to selective culture in the presence of at least about 100 nM methotrexate as a selecting agent to produce a clone of isolated transfectants essentially free of nontransfected mammalian cells;

(c) culturing said clone in the absence of methotrexate; and (d) treating said cultured clone with methotrexate at a concentration sufficient to induce, in less than the cell doubling time of said cultured clone, an increase in transcription coordinately of the genes carried on said vector and encoding DHFR and said protein of interest.

2. In a method for producing a protein of interest in a host cell, said method relying on DHFR selection for a transfectant of a mammalian cell, said transfectant harboring an expression vector comprising a first transcription unit comprising an expressible gene encoding an enzymatically functional dihydrofolate reductase (DHFR) and a second transcription unit comprising an expressible gene encoding a protein of interest, said transfectant being isolated from nontransfected cells by selective culture using methotrexate as a selective agent, the improvement comprising the steps of:

(a) contacting said mammalian cell with a said expression vector under conditions suitable for transfection of said cell with at least about 100 copies of said vector, such that a transfectant of said mammalian cell is produced;

(b) subjecting said transfectant to selective culture in the presence of at least 100 nM methotrexate as a selecting agent to produce a clone of isolated transfectants essentially free of nontransfected mammalian cells;

(c) culturing said clone in the absence of methotrexate; and (d) treating said cultured clone with methotrexate at a concentration sufficient to induce, in less than the cell doubling time of said cultured clone, an increase in transcription coordinately of the genes carried on said vector and encoding DHFR and said protein of interest.

3. A method of inducing transcription of a gene encoding a protein of interest in a host cell, said gene being present in a DHFR-selectable expression vector, comprising the steps of:

(a) contacting a mammalian cell with an expression vector comprising a first transcription unit comprising an expressible gene encoding an enzymatically functional dihydrofolate reductase (DHFR) and a second transcription unit comprising an expressible gene encoding a protein of interest, under conditions suitable for transfection of said cell with at least about 100 copies of said vector, such that a transfectant of said mammalian cell is produced;

(b) subjecting said transfectant to selective culture in the presence of at least about 100 nM methotrexate as a selecting agent to produce a clone of isolated transfectants essentially free of nontransfected mammalian cells;

(c) analyzing said clone to determine the copy number of expression vector present therein;

(d) culturing said clone in the absence of methotrexate; and (e) treating said cultured clone with methotrexate under conditions sufficient to induce an increase in transcription coordinately of the genes carried on said expression vector and encoding DHFR and said protein of interest, said conditions being insufficient to induce a detectable amplification of the copy number of said vector.

4. The method of claim 1 or 2 wherein said cultured clone is treated with methotrexate in step (d) at a concentration sufficient to induce at least a two-fold increase coordinately in the transcription of said genes.

5. The method of claim 1, 2 or 3 wherein said transfectant is subjected to selective culture in step (b) in the presence of serially increasing concentrations of MTX.

6. The method of claim 1, 2 or 3 wherein said transfectant is produced in step (a) by protoplast or spheroplast fusion.

7. The method of claim 1, 2 or 3 wherein said expression vector further comprises an enhancer element.

8. The method of claim 1, 2 or 3 wherein the DHFR encoded by said gene is a mutein having reduced MTX-binding affinity relative to wild type DHFR, and said cell contains a wild type DHFR gene.

9. The method of claim 1, 2 or 3 wherein said mammalian cell is a myeloma.

10. The method of claim 1, 2 or 3 wherein said gene encoding a protein of interest encodes a protein selected from the group consisting of peptide hormones, interleukins, tissue plasminogen activator, pro-urokinase, immunoglobulin, and active analogs, fragments, derivatives, and fusion products thereof.

11. The method of claim 1, 2 or 3 wherein said gene encoding a protein of interest encodes an immunoglobulin selected from the group consisting of human light chain, human heavy chain, murine light chain, murine heavy chain, chimeric murine-human light chain, and chimeric murine-human heavy chain.

12. The method of claim 3 wherein said cultured clone is treated with methotrexate in step (e) under conditions sufficient to induce a greater than ten-fold increase in the transcription of said gene encoding said protein of interest.

13. The method of claim 5 wherein said concentrations of MTX are increased 5-fold at less than two week intervals.

14. The method of claim 5 wherein the MTX concentration is raised serially from about 100 nM to at least 1 µM.

15. The method of claim 14 wherein the MTX concentration is raised serially to at least 5 µM.

16. The method of claim 15 wherein the MTX concentration is raised serially to at least 20 µM.

17. The method of claim 7 wherein said expression vector further comprises a blocking element interposed between said DHFR gene and said gene encoding said protein of interest.

18. The method of claim 17 wherein said blocking element is the lambda light chain promoter.

19. The method of claim 8 wherein the mutein of DHFR encoded by said gene is 3T6-R400 DHFR.

20. The method of claim 9 wherein said mammalian cell is a murine cell.

* * * * *